United States Patent [19]

Brenner

[11] 4,282,227
[45] Aug. 4, 1981

[54] RENAL VASODILATING 3,4-DIHYDROXYPHENYLTETRAHYDRO-THIENOPYRIDINES

[75] Inventor: L. Martin Brenner, Havertown, Pa.
[73] Assignee: SmithKline Corporation, Philadelphia, Pa.
[21] Appl. No.: 152,253
[22] Filed: May 22, 1980
[51] Int. Cl.³ .................... A61K 31/44; C07D 495/04
[52] U.S. Cl. ........................................ 424/256; 546/80; 546/114; 549/29; 549/49; 549/58; 549/65; 549/81
[58] Field of Search .................... 546/114, 80; 424/256

[56] References Cited

U.S. PATENT DOCUMENTS

| 3,520,895 | 7/1970 | Suh ........................................ 546/80 |
| 4,104,390 | 8/1978 | Ferrand et al. ...................... 546/114 |
| 4,172,134 | 10/1979 | Fréhel et al. .......................... 546/80 |

FOREIGN PATENT DOCUMENTS

| 856732 | 1/1978 | Belgium .................................. 546/114 |
| 871247 | 4/1978 | Belgium .................................. 546/114 |
| 108 | 12/1978 | European Pat. Off. .................. 546/80 |

Primary Examiner—Richard A. Schwartz
Attorney, Agent, or Firm—William H. Edgerton; Richard D. Foggio; Alan D. Lourie

[57] ABSTRACT 3,4-Dihydroxyphenyltetrahydrothieno[2,3-c] or [3,2-c] pyridines are prepared by cyclization of a N-thienylmethyl-2-(3',4'-dimethoxyphenyl)-ethanolamine. These compounds have renal vasodilating activity. A species is 4-(3,4-dihydroxyphenyl)-1,2,3,4-tetrahydrothieno[2,3-c]pyridine and its pharmaceutically acceptable acid addition salts or esters.

8 Claims, No Drawings

RENAL VASODILATING 3,4-DIHYDROXYPHENYLTETRAHYDRO-THIENOPYRIDINES

This invention relates to a new group of chemical compounds having renal vasodilating activity whose structures are characterized by having a tetrahydrothieno[2,3-c] or [3,2-c] pyridine nucleus with a 3,4-dihydroxyphenyl substituted at the 4 or 7 position respectively.

DESCRIPTION OF THE PRIOR ART

U.S. Pat. No. 4,104,309 and its Belgian counterpart application No. 856,732 describe tetrahydrothieno[2,3-c] or [3,2-c]pyridines having 4 or 7-phenyl which may be unsubstituted or substituted by a halo, hydroxy, alkyl or alkoxy which have antiinflammatory and blood platelet aggregation inhibiting activity. Belgian application No. 871,247 describes a more limited group of 4-phenyltetrahydro[2,3-c]pyridines which have antidepressant activity. U.S. Pat. No. 4,172,134 and its EPO counterpart application No. 108 discloses similar benzo[b]thienopyridines which have blood platelet aggregation inhibiting and sedative activities. None of these references discloses the specific 3,4-dihydroxyphenyl substituted tetrahydrothienopyridines of this invention or their renal dilating activity.

DESCRIPTION OF THE INVENTION

The new compounds of this invention are represented by the following three structural formulas:

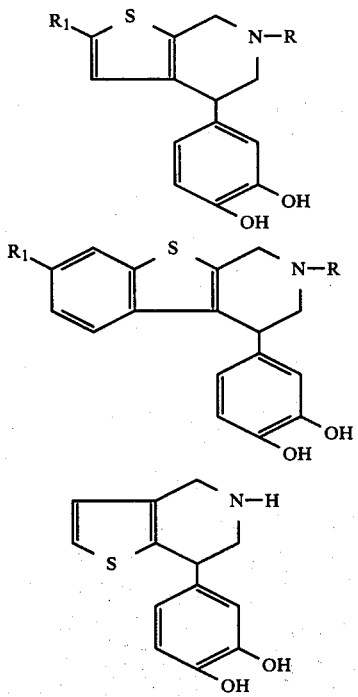

in which R is hydrogen or methyl and $R_1$ is halo or hydrogen.

Of these compounds those of Formula I demonstrate more potent renal vasodilating activity and of these the compound in which R is hydrogen is about 10 times more active than the compound in which R is methyl.

Included in this invention along with the basic compounds of Structures I–III are the pharmaceutically acceptable salts of the bases with non-toxic organic and inorganic acids such as hydrochloric, hydrobromic, sulfuric, phosphoric, methane sulfonic, maleic, tartaric, citric, sulfamic or ethane disulfonic acids. The salts are easily prepared by reacting the base with a slight stoichiometric excess of acid in an organic solvent. The salt either separates directly and in good yield or is recovered by evaporating the solvent.

Other phenolic derivatives known to the art to be degraded in vivo to give the active dihydroxy parent compounds are also alternatives to the present compounds such as the di-O-lower alkanoyl esters of 2–8 carbons each or the lower alkyl ethers of 1–6 carbons each.

The compounds of this invention are prepared most conveniently by the following reacting sequence or modifications thereof.

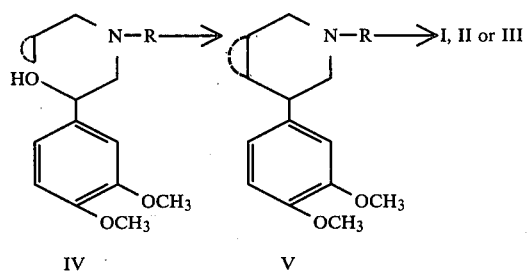

in which the partial structures are the thieno or benzothieno rings of I, II or III and R is hydrogen or methyl.

The cyclization (IV→V) is carried out by reaction of the appropriate N-thienylmethyl-2-(3,4-dimethoxyphenyl)-ethanolamine with a Lewis acid cyclizing agent such as boron trifluoride, stannous chloride or aluminum chloride or an acid cyclizing agent such as trifluoroacetic acid, sulfuric acid, polyphosphorous acid or trifluoromethylsulfonic acid. The catecholic protective groups are then removed by using a dealkylating agent, for example, boron tribromide, an excess of aluminum chloride, hydrohalic acid complexes such as pyridine hydrochloride, hydriodic acid, boron trichloride or hydrobromic acid.

BIOLOGICAL ACTIVITY OF THE COMPOUNDS

The renal dilating activity of the compounds of this invention is demonstrated by a known pharmacological procedure in which mean arterial blood pressure (MAP), renal blood flow (RBF), renal vascular resistance (RVR) and heart rate (HR) are monitored in a normotensive anesthetized dog after infusion of the test compound in μg/kg/min doses of 5 minutes duration. Usually the dose concentrations are 3, 30 and 300 μg/kg/min. Dopamine at 3 μg/kg/min is the positive control. An increased renal blood flow and a decreased renal vascular resistance indicate a renal vasodilatation. This end result is useful for improving kidney function and for treating abnormal cardiovascular conditions such as hypertension optionally in conjunction with other known cardiovascular drugs.

| (A) 4-(3,4-Dihydroxyphenyl)-4,5,6,7-tetrahydrothieno-[2,3-c]pyridine hydrobromide | | | | |
|---|---|---|---|---|
| | % Change from Control | | | |
| Dose | MAP | RBF | RVR | HR |

-continued

| Dopamine | 3 | −5.0 | +36.5* | −30.0* | 0 |
|---|---|---|---|---|---|
| A | 3 | −0.5 | +12.0* | −11.5* | 0 |
|   | 30 | −7.0 | +35.0* | −31.0* | +13.5* |
|   | 300 | −16.5* | +14.5* | −27.5* | +20.0* | n of dogs = 2
secondary test $ED_{15}$ = 21 µg/kg (B) 4-(3,4-Dihydroxyphenyl)-6-methyl-4,5,6,7-tetrahydrothieno-[2,3-c]pyridine hydrobromide

| | | % Change from Control | | |
|---|---|---|---|---|
| | Dose | MAP | RBF | RVR | HR |
| Dopamine | 3 | −7.7* | +19.0* | −22.9* | +3.4 |
| B | 3 | +4.2* | 0 | +4.2 | 0 |
|   | 30 | −2.6 | +38.5* | −29.7* | +5.1 |
|   | 300 | −36.4* | +52.5* | −56.0* | −15.2* | n = 2
$ED_{15}$ = 211 µg/kg (C) 4-(3,4-Dihydroxyphenyl)-2-methyl-4,5,6,7-tetrahydro-benzo[b]thieno[2,3-c]pyridine hydrobromide

| | | % Change from Control | | |
|---|---|---|---|---|
| | Dose | MAP | RBF | RVR | HR |
| Dopamine | 3 | −5.0 | +36.0* | −29.5* | +1.0 |
| C | 3 | −1.0 | +9.0* | −9.5* | 0 |
|   | 30 | +1.0 | +10.0* | −8.0 | 0 |
|   | 300 | +2.5 | −3.5 | +6.5 | 1.0 | n = 2

(D) 7-(3,4-Dihydroxyphenyl)-4,5,6,7-tetrahydrothieno[3,2-c]-pyridine hydrobromide

| | | % Change from Control | | |
|---|---|---|---|---|
| | Dose | MAP | RBF | RVR | HR |
| Dopamine | 3 | 5.0 | +10.0* | −10.0* | +3.5 |
| D | 3 | −0.5 | +1.5 | −4.5 | +2.0 |
|   | 30 | −5.0 | +13.0* | −13.0* | +5.5 |
|   | 300 | −50.5* | −50.0* | +1.0 | +3.5 | n = 2
Pressor effects at 300 µg/kg/min

Compound A did not significantly affect parameters monitored in the phosphate-mannitol renal clearance tests in dogs at 10 mg/kg orally.

(E) 2-chloro-4-(3,4-dihydroxyphenyl)-6-methyl-4,5,6,7-tetra-hydrothieno[2,3-c]pyridine hydrobromide

| | | % Change from Control | | |
|---|---|---|---|---|
| | Dose | MAP | RBF | RVR | HR |
| Dopamine | 3 | −5.8* | +42.7* | −32.1* | −1.5 |
| E | 3 | 0 | 0 | 0 | 0 |
|   | 30 | +3.8 | +4.0 | −1.1 | +5.5 |
|   | 300 | −3.6 | +22.9* | −21.4* | −0.5 | n = 2

The pharmaceutical compositions of this invention having a renal vasodilatation activity and especially activity to treat hypertension or other abnormal cardiovascular conditions are prepared in conventional dosage unit forms by incorporating a compound of Formulas I, II or III or a pharmaceutically acceptable acid addition salt or ester thereof, with a nontoxic pharmaceutical carrier according to accepted procedures in a nontoxic amount sufficient to produce the desired pharmacodynamic activity in a subject in need thereof, animal or human. Preferably the compositions will contain the active ingredient in an effective but nontoxic amount selected from about 15 mg to about 500 mg preferably about 25–75 mg of active ingredient per dosage unit but this quantity depends on the relative potency of the basic compound, the specific biological activity desired, the route of administration, oral or parenteral, and the condition of the patient. The lead or preferred compounds (Compound A or B above) of this invention is preferably used in nontoxic and renal dilating quantities selected from the dosage unit range of from 25–250 mg of base given orally. Intravenous or subcutaneous doses of the compounds would be lower.

The dosage units may be tablets, capsules, troches, sterile solutions or suspensions for infusion or injection, suppositories, oral suspensions or solutions or oral sustained release forms all prepared and used as known to the art using the dosage unit and regimen quantities given as exemplary herein.

In the pharmacodynamic methods of this invention the compounds of Formulas I, II and III are given internally, preferably orally or parenterally, to a human or animal patient in need of renal dilatation such as a hypertensive patient in quantities sufficient to induce such activity and yet be nontoxic. While dopamine has a general activity both as receptors in the central nervous system as well as at peripheral receptors, the compounds of Formulas I, II, or III mimic dopamine at the receptors in the kidney. Generally the dosage units described above are administered to the patient from 1–6 times daily or even by infusion or in sustained release forms in order to maintain substantial levels of active ingredient in the body. A typical daily dose range is from 100 mg–1 g. of base.

The following examples are designed to illustrate the preparation and use of the new compounds of this invention. Other variations of this invention and these examples will be obvious to those skilled in the art. All temperatures are in degrees Centigrade.

EXAMPLE 1

A mixture of 2.24 g. (1.75 ml., 0.02 ml.) of thiophene-3-carboxaldehyde, 4.67 g. (0.02 m.) of 2-amino-1-(3,4-dimethoxyphenyl)ethanol hydrochloride, 1.6 ml. of triethylamine and 20 ml. of methanol was prepared and heated on the steam bath while stirring. After the mixture is brought to boiling, it was stirred at room temperature for 1 hour. Cooling separated 4.65 g. (80%) of the Schiff base product, m.p. 131°–133°.

Anal. Calc'd. for $C_{15}H_{17}NO_3S$: C, 61.83; H, 5.88; N, 4.81. Found: C, 62.18; H, 5.59; N, 4.84.

Sodium borohydride (0.46 g., 0.123 m.) was added in small portions to a stirred mixture of 4.77 (0.0164 m.) of the Schiff base and 30 ml. of methanol after stirring for 45 minutes, water was added to the mixture. The white solid was washed with water to give 4.47 g. (93%) of N-(3-methylthienyl)-1-(3,4-dimethoxyphenyl)-2-aminoethanol, m.p. 108°–109°.

Anal. Cald'd. for $C_{15}H_{19}NO_3S$: C, 61.41; H, 6.53; N, 4.77. Found: C, 61.34; H, 6.39; N, 4.75.

A mixture of 1.24 mole (0.0223 m) of concentrated sulfuric acid and 44 ml. of trifluoroacetic acid was added to the aminoethanol (4.36 g., 0.0149 m.). The mixture was stirred at room temperature for 0.5 hours. Excess volatiles were evaporated in vacuo. Ice was added to the syrup residue then water. A white solid formed. The mixture was taken to pH 11 then filtered. The solid was washed with water and air dried to give 3.92 g. (96%) of 7-(3,4-dimethoxyphenyl)-4,5,6,7-tetrahydrothieno-[3,2-c]pyridine, m.p. 118°–120°. This material was taken through chloroform, washed, dried and recrystallized with no change in melting point.

This base (0.5 g., 0.00182 m.) was dissolved in methanol and treated with ethereal hydrogen chloride to give the hydrochloride salt, m.p. 250°–252°.

A mixture of 3.41 g. (0.0136 m.) of boron tribromide and 25 ml. of dry methylene chloride was added slowly to a stirred solution of 0.75 g. (0.00272 m.) of the dimethoxy base at −20° under nitrogen. The mixture was then allowed to come to room temperature and was stirred for two hours then cooled while 15 ml. of methanol was added slowly. About 50 ml. of solvent was taken off and 50 ml. of methanol again added. The mixture was concentrated to 15 ml. After repeating the quenching process twice, 40 ml. of ethanol was added. The methanol was distilled off until a solid began to crystallize. Chilling produced 0.92 g. of 7-(3,4-dihydroxyphenyl)4,5,6,7-tetrahydrothieno[3,2-c]pyridine hydrobromide, m.p. 234°–237°.

Anal. Calc'd. for $C_{13}H_{13}NO_2S$: C, 47.57; H, 4.30; N, 4.27 Found C, 47.91; H, 4.30; N, 4.31

This material (200 mg.) is mixed with 100 g. of lactose and 2 mg. of magnesium stearate then filled into a hard gelatin capsule which is administered 4 times daily to a hypertensive patient.

EXAMPLE 2

Following the reaction sequence of Example 1 but using 1.2 g. (0.0107 m.) of 2-thiophenecarboxaldehyde gives 2.55 g. (82%) of the Schiff base, m.p. 112°–114°.

Anal. Calc'd. for $C_{15}H_{17}NO_3S$: C, 61.83; H, 5.88; N, 4.81 Found: C, 61.79; H, 5.77; N, 4.79

The Schiff base (2.4 g., 0.00823 m.) was reduced using 0.23 g. (0.00618 m.) of sodium borohydride in 15 ml. of methanol to give 1.95 g. (81%) of N-(2-methylthienyl)-1(3,4-dimethoxyphenyly)-2-aminoethanol, m.p. 77°–79°.

Anal. Calc'd. for $C_{15}H_{19}NO_3S$: C, 61.41; H, 6.53; N, 4.77 Found: C, 61.43; H, 6.27; N, 4.80.

The aminoethanol (1.88 g., 0.00641 m.) is cyclized by reaction with 0.53 ml. (0.00861 m.) of sulfuric acid and 19 ml. of trifluoroacetic acid to give 1.55 g. (88%) of 4-(3,4-dimethoxyphenyl)-4,5,6,7-tetrahydrothieno[2,3-c]pyridine, m.p. 115°–117°. The hydrochloride salt melts at 210°–215°.

Anal. Calc'd. for $C_{15}H_{17}NO_3S$. HCl: C, 57.78; H, 5.82; N, 4.49 Found: C, 57.45; H, 6.05; N, 4.42.

The basic solid (0.6 g., 0.00218 m.) was demethylated using 1.03 ml. (0.0109 m.) of boron tribromide in 25 ml. of dry methylene chloride to give 0.68 g. (94%) of 4-(3,4-dihydroxyphenyl)-4,5,6,7-tetrahydro[2,3-c]pyridine hydrobromide, m.p. 233°–237°.

Anal. Calc'd. for $C_{13}H_{13}NO_2S$.HBr: C, 47.57; H, 4.30; N, 4.27 Found: C, 47.68; H, 4.38; N, 4.13

This reaction sequence was also repeated on a larger scale with comparable results.

This salt (100 mg.) is mixed with 250 mg. of lactose and 2 mg. of magnesium stearate, filled into a capsule which is given orally 5 times a day to a hypertensive patient.

EXAMPLE 3

A mixture of 2.7 g. (0.0137 m.) of 1-(3,4-dimethoxyphenyl)-2-(methylamino)ethanol, 3.0 g. (0.0142 m.) of 2-chloro-5-bromomethylthiophene, (prepared by reduction of 2-chlorothiophene-5-carboxaldehyde with hydrazine to give 2-chloro-5-methylthiophene followed by bromination using N-bromosuccinimide), 4.7 g. of potassium carbonate and 45 ml. of dimethylformamide was heated at 70° on a steam bath overnight. The mixture was filtered, washed and evaporated to give a dark oil which was put over a silica gel column in chloroform-methanol (1%) to give 2.6 g. (56%) of the dark oily aminoethanol.

This material (2.6 g., 0.0076 m.) was stirred in trifluoroacetic acid at room temperature for 4 hours. The mixture is quenched, made basic and extracted into chloroform. After washing and drying the extracts are combined and evaporated. The residue is taken up in dry ether and hydrogen chloride added to give 1.22 g. (45%) of 2-chloro-4-(3,4-dimethoxyphenyl)-6-methyl-4,5,6,7-tetrahydrothieno[2,3-c]pyridine hydrochloride, m.p. 225°–230° (d).

The dimethoxy compound (1.15 g., 0.0032 m.) in 54 ml. of methylene chloride is mixed with 1.8 ml. of boron tribromide in 22 ml. of methylene chloride. Reaction and working up the mixture as described gave 270 mg. (21%) for 2-chloro-4-(3,4-dihydroxyphenyl)-6-methyl-4,5,6,7-tetrahydrothieno[2,3-c]pyridine hydrobromide, m.p. 258°–264° (d).

Anal. Calc'd. for $C_{14}H_{14}ClNO_2S.HBr$: C, 44.64; H, 4.01; N, 3.72 Found: C, 44.44; H, 4.23; N, 3.59.

The hydrobromide (500 mg.) is shaken in carbonate-ether. The ether layer is separated and dried. One aliquot is evaporated to give the base (200 mg.). The other aliquot is reacted with a slight excess of methane sulfonic acid to give the methane sulfonic acid salt (250 mg.).

The latter salt (175 mg.) is combined with 125 mg. of lactose and filled into a capsule which is administered orally to a patient in need of improved kidney function from 3–5 times daily.

Substituting 2-fluoro-5-methylthiophene or 2-bromo-5-methylthiophene in the above reaction sequence gives 2-fluoro-4-(3,4-dihydroxyphenyl)-6-methyl-4,5,6,7-tetrahydrothieno[2,3-c]pyridine hydrochloride and 2-bromo-4-(3,4-dihydroxyphenyl)-6-methyl-4,5,6,7-tetrahydrothieno[2,3-c]pyridine hydrobromide.

EXAMPLE 4

A mixture of 3.5 g. (0.02 m.) of 2-bromomethylthiophene, 5.0 g. (0.02 m.) of 1-(3,4-dimethoxyphenyl)-2-(methylamino)ethanol hydrochloride, 13 g. of potassium carbonate and 70 ml. of dimethylformamide was stirred overnight at 70° under nitrogen. After evaporation, washing and extraction a dark oil was obtained which was purified over a silica gel column in a chloroform slurry to give 4.5 g. (33%) of oily secondary amine. This material (2 g., 0.0065 m.) was heated at reflux in 75 ml. of trifluoroacetic acid to give, after working up as above 1.24 g. (59%) of solid 4-(3,4-dimethoxyphenyl)-6-methyl-4,5,6,7-tetrahydrothieno[2,3-c]pyridine, m.p. 220°–222°.

The dimethoxy compound (2.4 g., 0.0074 m.) in 125 ml. of methylene chloride at −30° was reacted with 4.1 ml. (0.03 m.) of boron tribromide. Quenching with methanol and working up as described above gave 1.63 g. (65%) of 4-(3,4-dihydroxyphenyl)-6-methyl-4,5,6,7-tetrahydrothieno[2,3-c]pyridine hydrobromide, m.p. 259°–263° (d).

Anal. Calc'd. for $C_{14}H_{15}NO_2S.HBr$: C, 49.13; H, 4.71; N, 4.09 Found: C, 49.42; H, 4.63; N, 4.11.

This compound (250 mg.) is mixed with 100 mg. of lactose and 2 mg. of magnesium stearate then filled into a capsule which is administered three times daily to a hypertensive patient.

EXAMPLE 5

A mixture of 4 g. (0.026 m.) of 2-methylbenzothiophene, 4.7 g. (0.027 m.) of N-bromosuccinimide, a catalytic amount of benzoyl peroxide and 250 ml. of carbon tetrachloride was stirred under irradiation for 30 minutes. The cooled and filtered mixture was evaporated to give an oily 2-bromomethylbenzothiophene.

A mixture of 3.4 g. (0.015 m.) of the bromide, 3.2 g. (0.013 m.) of 1-(3,4-dimethoxyphenyl)-2-(methylamino)ethanol hydrochloride, 9.0 g. of potassium carbonate and 45 ml. of dimethylformamide was stirred with heating at 70° under nitrogen overnight. The mixture was filtered. The carbonate cake was washed with hot dimethylformamide. The organic extract was evaporated. After adding water, the mixture was extracted three times with chloroform which was then backwashed with water, brine and dried. Evaporation gave a dark oil which was passed over silica gel with chloroform to give 4.7 g. (91%) of dark oil which crystallized to 3.1 g. of yellow solid tertiary amine, m.p. 107°–109°.

This material (3.1 g.) was stirred at room temperature in 60 ml. of trifluoroacetic acid-1.6 ml. of concentrated sulfuric acid. The trifluoroacetic acid was evaporated under vacuo. Ice then water was added to the residue. The water mixture was made basic to pH 11 then extracted with chloroform. The extract was washed with brine, water, brine and dried. Evaporation gave an oil which was converted to 2.85 g. (95%) of 4-(3,4-dimethoxyphenyl)-2-methyl-1,2,3,4-tetrahydrobenzo[b]-thieno[2,3-c]pyridine hydrochloride, m.p. 259°–262°, with ether-hydrogen chloride.

This material, 1.25 g. (0.0033 m.), was treated with 1.5 ml. of boron tribromide in 65 ml. of methylene chloride at −30° to give 1.29 (92%) of solid, 4-(3,4-dihydroxyphenyl)-2-methyl-1,2,3,4-tetrahydrobenzo[b]thieno[2,3-c]pyridine hydrobromide, m.p. 187°–194°.

Anal. Calc'd. for $C_{18}H_{17}NO_2S \cdot HBr$: C, 55.11; H, 4.62; N, 3.57 Found: C, 55.04; H, 4.61; N, 3.55

This material (150 mg.) is filled into a capsule with 200 mg. of lactose then administered 4 times daily to a patient in need of renal vasodilatation.

Repeating the above reaction sequence with a 3-bromomethyl-5-chloro-benzo[b]thiophene (U.S. Pat. No. 4,172,134) and N-methyl-3',4',-dimethoxy-2-hydroxyphenethylamine hydrochloride gives 8-chloro-2-methyl-4-(3,4-dihydroxyphenyl)-1,2,3,4-tetrahydrobenzo[b]thieno[3,2-c]pyridine hydrochloride.

What is claimed is:

1. A chemical compound of the formula:

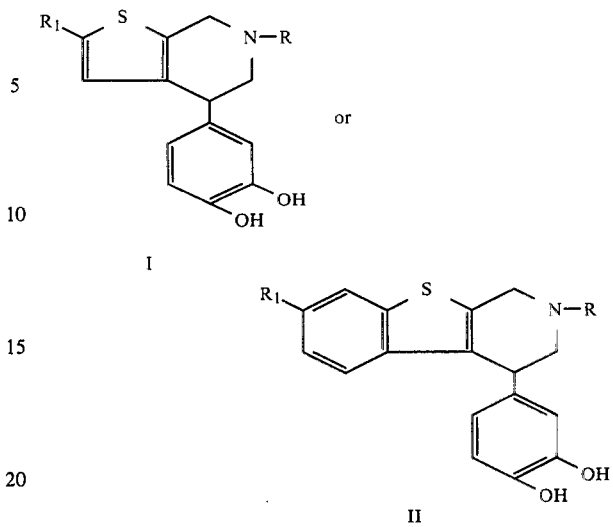

in which R is hydrogen or methyl and $R_1$ is hydrogen or halo; or a pharmaceutically acceptable acid addition salt thereof.

2. The compound of claim 1 in which the formula is that of structure I.

3. The compound of claim 1 in which the compound is 4-(3,4-dihydroxyphenyl)-4,5,6,7-tetrahydrothieno[2,3-c]pyridine or one of its pharmaceutically acceptable acid addition salts.

4. The compound of claim 1 in which the compound is 4-(3,4-dihydroxyphenyl)-6-methyl-4,5,6,7-tetrahydrothieno[2,3-c]pyridine or one of its pharmaceutically acceptable acid addition salts.

5. The compound of claim 1 in which the compound is 4-(3,4-dihydroxyphenyl)-6-methyl-4,5,6,7-tetrahydrothieno[2,3-c]pyridine as the base.

6. The compound of claim 1 in which the compound is 4-(3,4-dihydroxyphenyl)-6-methyl-4,5,6,7-tetrahydrothieno[2,3-c]pyridine as one of its hydrohalide salts.

7. A pharmaceutical composition having renal dilating activity comprising a pharmaceutical carrier in dosage unit form and a pharmaceutically effective quantity of a compound of claims 1, 3 or 4.

8. The method of producing renal vasodilatation in a patient in need thereof comprising administering orally or parenterally to said patient a renal vasodilating but nontoxic quantity of a compound of claims 1, 3 or 4.

* * * * *